(12) United States Patent
Yang et al.

(10) Patent No.: US 9,012,660 B2
(45) Date of Patent: Apr. 21, 2015

(54) 5,6,7,8-TETRAHYDRO-6-[N,N-BIS [(2-THIENYL)ETHYL]] AMINO-1-NAPHTHOL, AND PREPARING METHOD AND USE THEREOF

(75) Inventors: Mina Yang, Yantai (CN); Yanyan Zhao, Yantai (CN); Fengmei Zhou, Yantai (CN); Quingguo Meng, Yantai (CN); Tao Wang, Yantai (CN)

(73) Assignee: Shandong Luye Pharmaceutical Co., Ltd. (CN)

( * ) Notice: Subject to any disclaimer, the term of this patent is extended or adjusted under 35 U.S.C. 154(b) by 0 days.

(21) Appl. No.: 14/238,936

(22) PCT Filed: Aug. 6, 2012

(86) PCT No.: PCT/CN2012/001038
§ 371 (c)(1),
(2), (4) Date: Feb. 14, 2014

(87) PCT Pub. No.: WO2013/023433
PCT Pub. Date: Feb. 21, 2013

(65) Prior Publication Data
US 2014/0196523 A1 Jul. 17, 2014

(30) Foreign Application Priority Data
Aug. 17, 2011 (CN) .......................... 2011 1 0235541

(51) Int. Cl.
*C07D 333/20* (2006.01)
*G01N 30/02* (2006.01)
*C07D 409/12* (2006.01)
*G01N 30/88* (2006.01)

(52) U.S. Cl.
CPC ............ *C07D 333/20* (2013.01); *C07D 409/12* (2013.01); *G01N 2030/8877* (2013.01); *G01N 30/02* (2013.01)

(58) Field of Classification Search
USPC ...................................... 73/61.52; 549/59, 75
See application file for complete search history.

(56) References Cited

U.S. PATENT DOCUMENTS 4,564,628 A 1/1986 Horn

OTHER PUBLICATIONS

Gerding et al., Determination of enantiomeric purity of the new D-2 dopamine agonist 2-(N-propyl-N-2-thienylethylamino)-5-hydroxytetralin (N-0437) by reversed-phase high-performance liquid chromatography after pre-column derivatization with D(+)-glucuronic acid, Journal of Chromatography, Biomedical Applications, 1989, vol. 487, No. 1, 125-34.*
International Search Report for Application No. PCT/CN2012/001038 dated Nov. 29, 2012.
International Written Opinion for Application No. PCT/CN2012/001038 dated Nov. 29, 2012.

* cited by examiner

*Primary Examiner* — Kristin Vajda
(74) *Attorney, Agent, or Firm* — Lerner, David, Littenberg, Krumholz & Mentlik, LLP

(57) ABSTRACT

The present disclosure relates to 5,6,7,8-tetrahydro-6-[N,N-bis[(2-thienyl)ethyl]]amino-1-naphthol, a method for preparing the same, and use of 5,6,7,8-tetrahydro-6-[N,N-bis[(2-thienyl)ethyl]]amino-1-naphthol as a reference compound for determining an impurity in rotigotine or a preparation thereof.

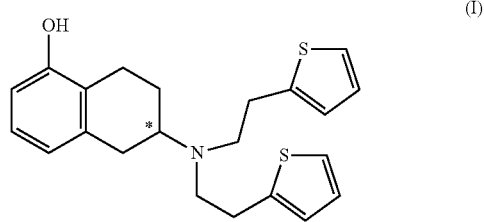

(I)

7 Claims, 2 Drawing Sheets

5,6,7,8-TETRAHYDRO-6-[N,N-BIS[(2-THIENYL)ETHYL]]AMINO-1-NAPHTHOL, AND PREPARING METHOD AND USE THEREOF

FIELD

The present disclosure belongs to the medical field, and more particularly relates to a reference compound for determining impurities in rotigotine or a preparation thereof, as well as method for preparing the same.

BACKGROUND

Parkinson's disease is a common degenerative disease of the nervous system for the middle-aged and elderly. Dopamine receptor agonist is an important class of drugs used in treating Parkinson's disease. Currently, the dopamine receptor agonist in clinical use comprises dopamine agonist drugs such as rotigotine, pramipexole, ropinirole, pergolide, and cabergoline, etc.

Rotigotine, (S)-5,6,7,8-tetrahydro-6-[propyl[2-(2-thienyl)ethyl]amino]-1-naphthol, is represented by a molecular formula of $C_{19}H_{25}NOS$ and has the following structure. In May 2007, the U.S. FDA approved its listing under the trade name NeuPro for the adjuvant treatment of early secondary Parkinson's disease and advanced Parkinson's disease.

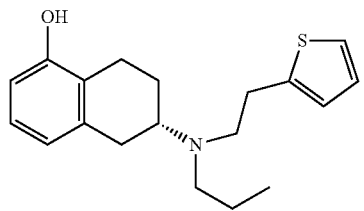 [SMILES: CCCN(CCc1cccs1)[C@H]1CCc2c(O)cccc2C1]

An impurity of a drug refers to a substance in the drug, which has no therapeutic effect but may influences the stability or efficacy of the drug, even may be harmful to human health. The source of the impurities mainly comprises the followings: firstly, the impurities that might have been introduced during the production process, including unreacted starting materials, chemical derivatives of impurities contained in the starting materials, synthesis by-products and degradation products; and secondly, the impurities that might have been produced during storage when the drug physico-chemical properties changed due to the external conditions. Adverse reactions produced in clinical use, in addition to being attributable to the pharmacological activity of the drug itself, sometimes may also be related to impurities present in the drug. Therefore, normative research on the impurity is directly related to the quality and safety of marketed drugs.

By understanding the chemical structure and synthetic pathway of the impurities and by identifying the parameters which affect the content of impurities in the end product, management of impurities in medicinal active substance may be greatly enhanced. To monitor the impurities in the medicinal active substance, it is required to establish a quality standard to determine suitable separation and detection conditions, so as to control the impurities well. In the quality standard, the currently widely used impurity detection methods mainly comprise high performance liquid chromatography (HPLC) and like.

SUMMARY

In one embodiment, the present disclosure provides a new, isolated compound as a reference compound for determining an impurity in rotigotine or a preparation thereof. The reference compound has a chemical name of 5,6,7,8-tetrahydro-6-[N,N-bis[(2-thienyl)ethyl]]amino-1-naphthol and is represented by formula (I):

compound of formula (I)

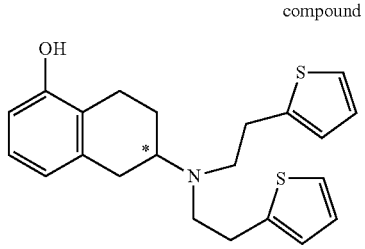

in which (*) represents a chiral center, and the compound of formula (I) is a R or S configuration or a racemic mixture.

The compound of formula (I) may be prepared by the following method, which comprises: reacting a compound of formula (II) with a compound of formula (III), and purifying the resulting compound of formula (I), compound of formula (II)

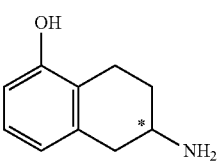

compound of formula (III)

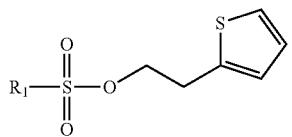

in which the compound of formula (II) is a R or S configuration or a racemic mixture, and $R_1$ is methyl, trifluoromethyl, methylphenyl or nitrophenyl, preferably 4-methylphenyl or 4-nitrophenyl, more preferably 4-methylphenyl.

The compound of formula (I) may be used as a reference compound for qualitatively or quantitatively determining an impurity in rotigotine or a preparation thereof, particularly, by high pressure liquid chromatography analysis. The compound of formula (I) is dissolved in a solution to prepare a reference solution. Rotigotine or the preparation thereof is dissolved in a solution to prepare a test solution. HPLC chromatograms of the reference solution and the test solution are obtained by high pressure liquid chromatography analysis respectively. The retention time in the HPLC chromatograms of the reference solution and the test solution are compared to determine the test solution contains the compound of formula (I). More specifically, the peak areas of the compound of formula (I) in the HPLC chromatograms of the reference solution and the test solution are compared, and the content of the compound of formula (I) in rotigotine or the preparation thereof in weight percent is determined by an external standard method.

In various embodiments, the isolated compound of formula (I) has a purity of at least 95%, preferably, the isolated compound of formula (I) has a purity of at least 98%; and more preferably, the isolated compound of formula (I) is free of any other compounds or impurities.

In a further embodiment, the present disclosure also provides a high-purity rotigotine, containing the compound of formula (I) in an amount less than 0.5 weight percent.

BRIEF DESCRIPTION OF THE DRAWINGS

FIG. 2-1 is an HPLC chromatogram of 5,6,7,8-tetrahydro-6-[N,N-bis[(2-thienyl)ethyl]]amino-1-naphthol.
FIG. 2-2 is an HPLC chromatogram of rotigotine.

DETAILED DESCRIPTION

Figure 1:
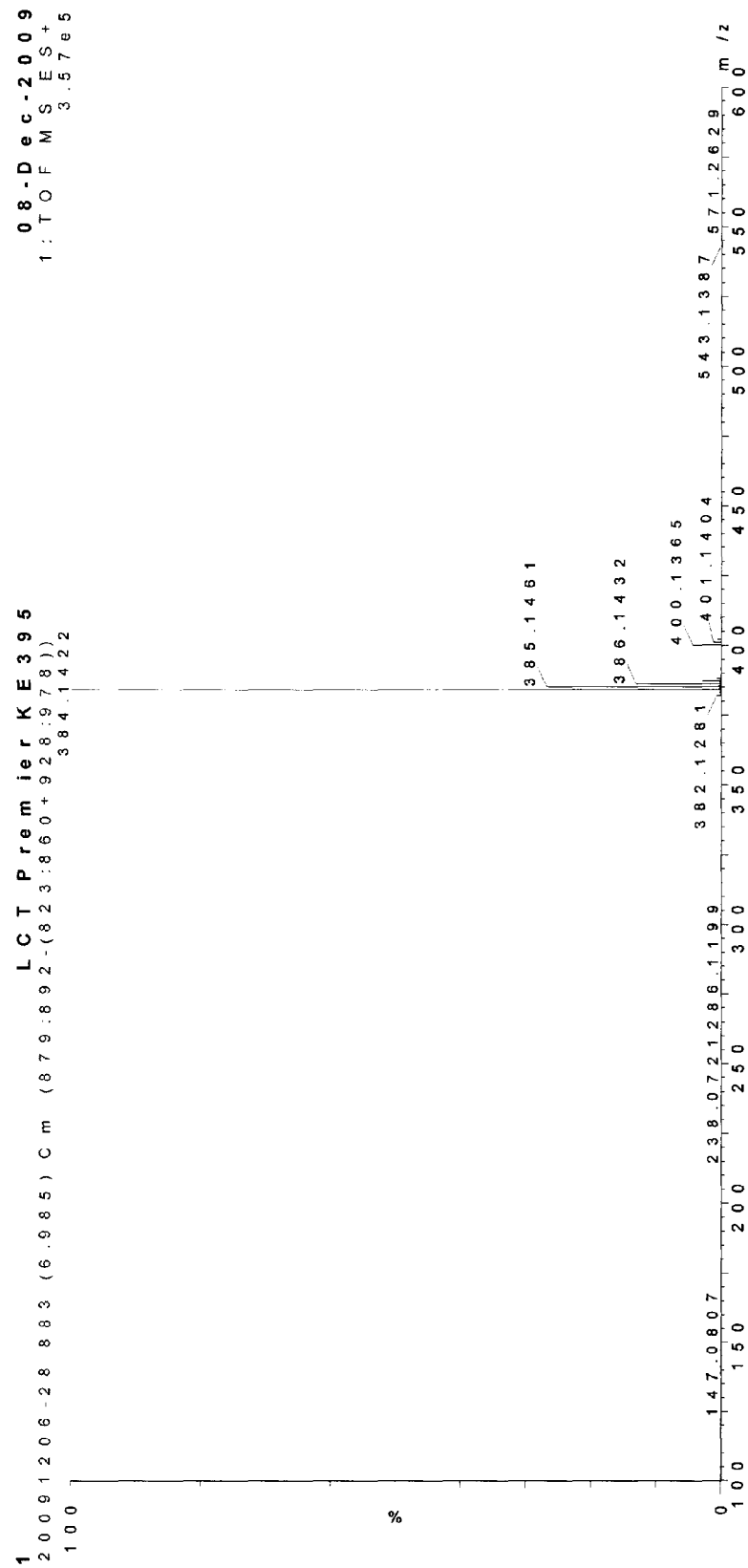
FIG. 1 is a high resolution mass spectrum of 5,6,7,8-tetrahydro-6-[N,N-bis[(2-thienyl)ethyl]]amino-1-naphthol.

One embodiment of the present disclosure provides a compound of formula (I):

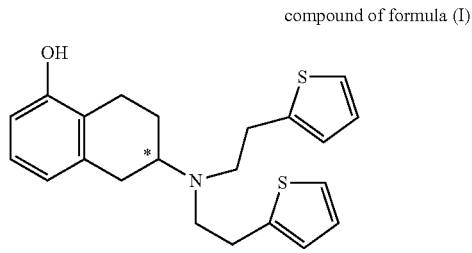 [SMILES: Oc1cccc2c1CCC(N(CCc1cccs1)CCc1cccs1)C2]

compound of formula (I)

wherein (*) represents a chiral center, and the compound of formula (I) is a R or S configuration or a racemic mixture.
In a further embodiment, the compound as used herein is isolated, i.e., the compound is at least 80%, preferably at least 90%, even more preferably at least 95%, and most preferably at least 99% pure, as judged by GC or HPLC.
Another embodiment of the present disclosure provides a method for preparing a compound of formula (I), comprising: reacting a compound of formula (II) with a compound of formula (III),

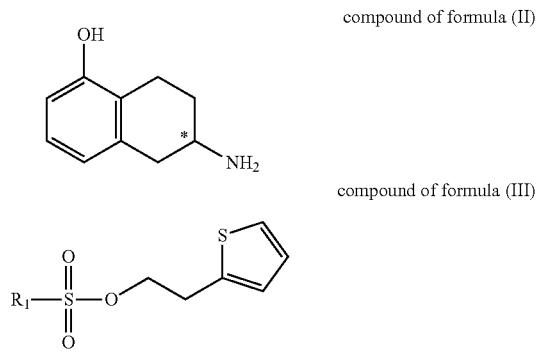

compound of formula (II)

compound of formula (III)

wherein the compound of formula (II) is a R or S configuration or a racemic mixture, and $R_1$ is methyl, trifluoromethyl, methylphenyl or nitrophenyl; and purifying the compound of formula (I).
In one preferred embodiment of the present disclosure, $R_1$ is 4-methylphenyl or 4-nitrophenyl.
In another preferred embodiment of the present disclosure, $R_1$ is 4-methylphenyl.
Another embodiment of the present disclosure provides the use of a compound of formula (I) as a reference compound for determining an impurity in rotigotine or a preparation thereof.

A further embodiment of the present disclosure provides a method for determining the content of an impurity in rotigotine or a preparation thereof by high pressure liquid chromatography analysis, wherein the compound of formula (I) is used as a reference compound, comprising: preparing a reference solution of the compound of formula (I) in a predetermined concentration; preparing a test solution containing rotigotine or a preparation thereof; obtaining HPLC chromatograms of the reference solution and the test solution by high pressure liquid chromatography analysis respectively; comparing respective retention times in the HPLC chromatograms of the reference solution and the test solution to ascertain that the test solution contains the compound of formula (I); and determining the content of the compound of formula (I) in rotigotine or the preparation thereof in weight percentage by an external standard method.
Yet another embodiment of the present disclosure provides a high-purity rotigotine, comprising rotigotine and a compound of formula (I) in an amount less than 0.5 weight percent.

EXAMPLES

The present disclosure will be further illustrated by the following examples and test examples, which will not limit the scope of the present invention in any way.

Example 1

Preparation of 5,6,7,8-Tetrahydro-6-[N,N-bis[(2-thienyl)ethyl]]amino-1-naphthol 5.0 g of 5,6,7,8-tetrahydro-6-amino-1-naphthol, 3.0 g of 2-(2-thienyl)ethyl 4-methylbenzenesulfonate, 4.8 g of sodium carbonate and 100 ml of xylene were mixed to form a mixture, and the mixture was refluxed for 48 h. The mixture was cooled to room temperature, and washed with an appropriate amount of water. Active carbon was added to decolorize the mixture. The mixture was filtered and left standing. An organic phase was reserved and concentrated under vacuum to obtain a residue. The residue was purified by column chromatography to obtain 1.7 g of 5,6,7,8-tetra-hydro-6-[N,N-bis[(2-thienyl)ethyl]]amino-1-naphthol. Attributions of nuclear magnetic resonance (NMR) spectra of 5,6,7,8-tetrahydro-6[N,N-bis[(2-thienyl)ethyl]]amino-1-naphthol were shown in Table 1. A high resolution mass spectrum of 5,6,7,8-tetrahydro-6-[N,N-bis[(2-thienyl)ethyl]]amino-1-naphthol was shown in FIG. 1.

TABLE 1

Attributions of NMR Spectra of
5,6,7,8-Tetrahydro-6-[N,N-bis[(2-thienyl)ethyl]]amino-1-naphthol

| No. | $^1$H-NMR | $^{13}$C-NMR |
|---|---|---|
| 1 | — | 153.4 |
| 2 | 6.65 | 111.7 |
| 3 | 6.95 | 126.1 |
| 4 | 6.52 | 121.4 |
| 5 | 3.04, 2.79 | 32.5 |
| 6 | 2.74 | 69.6 |
| 7 | 1.57, 1.81 | 30.1 |
| 8 | 2.85, 2.88 | 23.6 |
| 9 | — | 122.7 |
| 10 | — | 138.2 |
| 1' | 2.74 | 52.5 |

TABLE 1-continued

Attributions of NMR Spectra of
5,6,7,8-Tetrahydro-6-[N,N-bis[(2-thienyl)ethyl]]amino-1-naphthol

| No. | $^1$H-NMR | $^{13}$C-NMR |
| --- | --- | --- |
| 2' | 2.55 | 25.3 |
| 3' | — | 142.6 |
| 4' | 6.80 | 124.4 |
| 5' | 6.92 | 126.8 |
| 6' | 7.11 | 123.3 |
| 1" | 2.74 | 56.7 |
| 2" | 2.55 | 25.7 |
| 3" | — | 142.6 |
| 4" | 6.80 | 124.7 |
| 5" | 6.92 | 126.6 |
| 6" | 7.11 | 123.4 |

The numbering of the carbon atoms in the NMR structure of 5,6,7,8-tetrahydro-6-[N,N-bis[(2-thienyl)ethyl]]amino-1-naphthol were as follows:

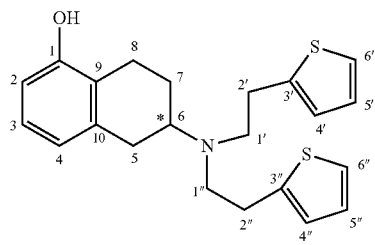 [SMILES: Oc1cccc2c1CCC(N(CCc1cccs1)CCc1cccs1)C2]

Example 2

Preparation of (S)-5,6,7,8-tetrahydro-6-[N,N-bis[(2-thienyl)ethyl]]amino-1-naphthol 5.0 g of (S)-5,6,7,8-tetrahydro-6-amino-1-naphthol, 3.0 g of 2-(2-thienyl)ethyl 4-methylbenzenesulfonate, 4.8 g of sodium carbonate and 100 ml of xylene were mixed to form a mixture, and the mixture was refluxed for 48 h to 50 h. The mixture was cooled to room temperature, and washed with an appropriate amount of water. Active carbon was added to decolorize the mixture. The mixture was filtered and left standing. An organic phase was reserved and concentrated under vacuum to obtain a residue. The residue was purified by column chromatography to obtain 1.7 g of (S)-5,6,7,8-tetrahydro-6-[N,N-bis[(2-thienyl)ethyl]]amino-1-naphthol. Attributions of nuclear magnetic resonance (NMR) spectra of (S)-5,6,7,8-tetrahydro-6-[N,N-bis[(2-thienyl)ethyl]]amino-1-naphthol were shown in Table 2.

TABLE 2

Attributions of NMR Spectra of
(S)-5,6,7,8-tetrahydro-6-[N,N-bis[(2-thienyl)ethyl]]amino-1-naphthol

| No. | $^1$H-NMR | $^{13}$C-NMR |
| --- | --- | --- |
| 1 | — | 153.5 |
| 2 | 6.66 | 111.9 |
| 3 | 6.97 | 126.4 |
| 4 | 6.56 | 121.6 |
| 5 | 3.04, 2.79 | 32.3 |
| 6 | 2.74 | 67.9 |
| 7 | 1.57, 1.83 | 30.1 |
| 8 | 2.85, 2.90 | 23.5 |
| 9 | — | 122.9 |
| 10 | — | 138.2 |
| 1' | 2.75 | 52.7 |
| 2' | 2.56 | 25.6 |
| 3' | — | 142.9 |
| 4' | 6.80 | 124.6 |
| 5' | 6.91 | 126.6 |
| 6' | 7.11 | 123.3 |
| 1" | 2.75 | 56.9 |
| 2" | 2.56 | 25.7 |
| 3" | — | 142.9 |
| 4" | 6.80 | 124.6 |
| 5" | 6.91 | 126.6 |
| 6" | 7.11 | 123.3 |

The numbering of the carbon atoms in the NMR structure of (S)-5,6,7,8-tetrahydro-6-[N,N-bis[(2-thienyl)ethyl]]amino-1-naphthol were as follows:

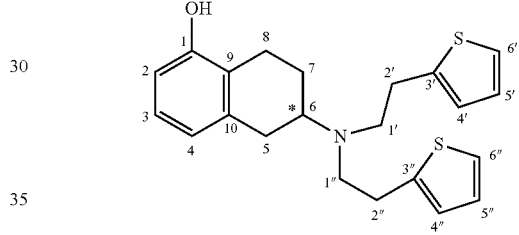

Example 3

Preparation of (S)-5,6,7,8-tetrahydro-6-[N,N-bis[(2-thienyl)ethyl]]amino-1-naphthol 5.0 g of (S)-5,6,7,8-tetrahydro-6-amino-1-naphthol, 3.3 g of 2-(2-thienyl)ethyl 4-methylbenzenesulfonate, 4.8 g of sodium carbonate and 100 ml of xylene were mixed to form a mixture, and the mixture was refluxed for 48 h to 50 h. The mixture was cooled to room temperature, and washed with an appropriate amount of water. Active carbon was added to decolorize the mixture. The mixture was filtered and left standing. An organic phase was reserved and concentrated under vacuum to obtain a residue. The residue was purified by column chromatography to obtain 1.5 g of (S)-5,6,7,8-tetrahydro-6[N,N-bis[(2-thienyl)ethyl]]amino-1-naphthol.

Example 4

Preparation of (S)-5,6,7,8-tetrahydro-6-[N,N-bis[(2-thienyl)ethyl]]amino-1-naphthol 5.0 g of (S)-5,6,7,8-tetrahydro-6-amino-1-naphthol, 2.2 g of 2-(2-thienyl)ethyl methane-sulfonate, 4.8 g of sodium carbonate and 100 ml of xylene were mixed to form a mixture, and the mixture was refluxed for 48 h to 50 h. The mixture was cooled to room temperature, and washed with an appropriate amount of water. Active carbon was added to decolorize the mixture. The mixture was filtered and left standing. An organic phase was reserved and concentrated under vacuum to obtain a residue. The residue was purified by column chromatography to obtain 1.3 g of (S)-5,6,7,8-tetrahydro-6-[N,N-bis[(2-thienyl)ethyl]]amino-1-naphthol.

Test Example 1

Use of 5,6,7,8-Tetrahydro-6-[N,N-bis[(2-thienyl) ethyl]]amino-1-naphthol as Reference Compound for Determining the Content of Impurity in Rotigotine Sample Preparation:

An appropriate amount of rotigotine was weighed and dissolved in an acetonitrile-0.05% methanesulfonic acid solution (20:80) to prepare a solution with a concentration of 1 mg/ml as a test solution. An appropriate amount of 5,6,7,8-tetrahydro-6-[N,N-bis[(2-thienyl)ethyl]]amino-1-naphthol was weighed precisely and dissolved in an acetonitrile-0.05% methanesulfonic acid solution (20:80) to prepare a solution, which was diluted quantitatively to prepare a solution with a concentration of 0.001 mg/ml as a reference solution.

Chromatographic Condition:

Stearyl bonded silica was used as a filler. A 0.05% methanesulfonic acid solution (0.5 ml of methanesulfonic acid was taken and diluted with water to 1000 ml) was used as a mobile phase A, acetonitrile/0.05% methanesulfonic acid (0.5 ml of methanesulfonic acid was taken and diluted with acetonitrile to 1000 ml) was used as a mobile phase B, and gradient elution was carried out according to the following table. The column temperature was 30° C. The detection wavelength was 220 nm. Theoretical plate number calculated by the rotigotine peak should not be less than 5000. 10 μl of the reference solution and 10 μl of the test solution were taken and injected into a high performance liquid chromatograph respectively.

| Mobile Phase Gradient | | |
|---|---|---|
| Time (min) | Mobile PhaseA (%) | Mobile PhaseB (%) |
| 0-2 | 95 | 5 |
| 35 | 40 | 60 |
| 35-38 | 40 | 60 |

Figures 1, 2:
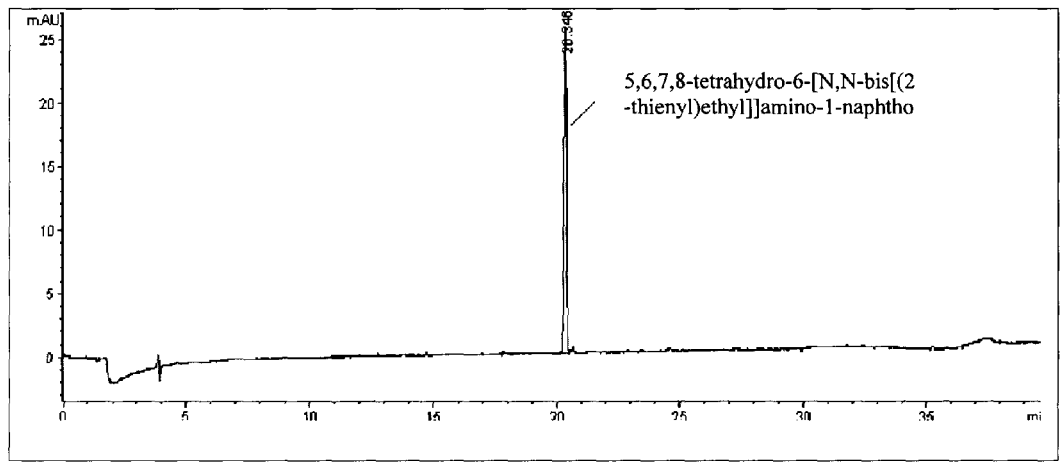
Figure 2:
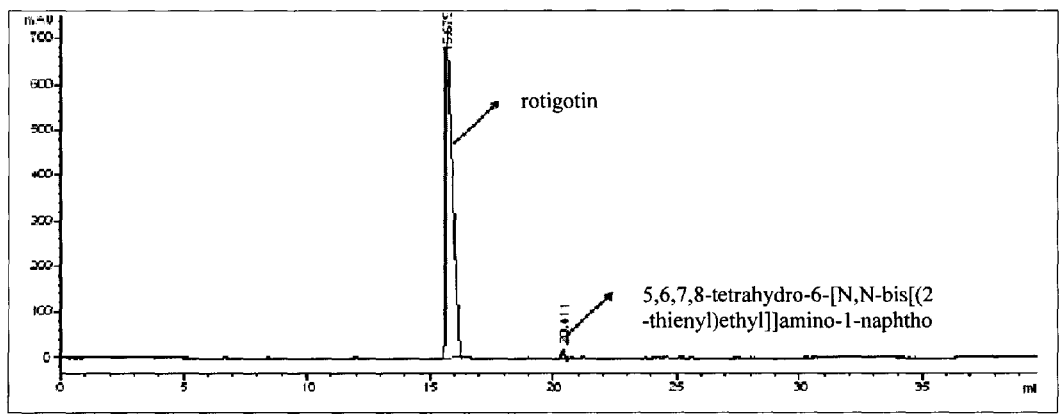

FIGS. 2-1 and 2-2 are HPLC chromatograms of 5,6,7,8-tetrahydro-6-[N,N-bis[(2-thienyl)ethyl]]amino-1-naphthol and rotigotine respectively. As calculated by the external standard method, in each of 3 batches of rotigotine, the content of 5,6,7,8-tetrahydro-6-[N,N-bis[(2-thienyl)ethyl]]amino-1-naphthol was lower than 0.5% in weight percent.

Test Example 2

Use of (S)-5,6,7,8-Tetrahydro-6-[N,N-bis[(2-thienyl) ethyl]]amino-1-naphthol as Reference Compound for Determining the Content of Impurity in Preparation of RotigotineMicrospheres Sample Preparation:

An appropriate amount of a rotigotine sustained release microspheres (equivalent to about 10 mg of rotigotine) were taken, weighed precisely and placed in a 10 ml volumetric flask. 5 ml of acetonitrile was added to dissolve the rotigotine to prepare a solution, which was diluted with a 0.01 mol/L hydrochloric acid solution to the scale so as to prepare a 10 ml solution of rotigotine. The 10 ml solution of rotigotine was shaken up and placed in a centrifuge tube. The centrifugal tube was centrifuged at a rotation speed of 13000 revolutions per minute for 5 minutes. The supernatant was taken and used as a test solution. An appropriate amount of (S)-5,6,7,8-tetrahydro-6-[N,N-bis[(2-thienyl)ethyl]]amino-1-naphthol was weighed precisely and dissolved in an acetonitrile-0.05% methanesulfonic acid solution (20:80) to prepare a solution, which was diluted quantitatively to prepare a solution with a concentration of 0.005 mg/ml as a reference solution.

Chromatographic Condition: the same as that in Test Example 1

As calculated by the external standard method, in each of 3 batches of rotigotine microspheres, the content of (S)-5,6,7, 8-tetrahydro-6[N,N-bis[(2-thienyl)ethyl]]amino-1-naphthol was lower than 0.5% in weight percent.

What is claimed is:

1. A compound of formula (I):

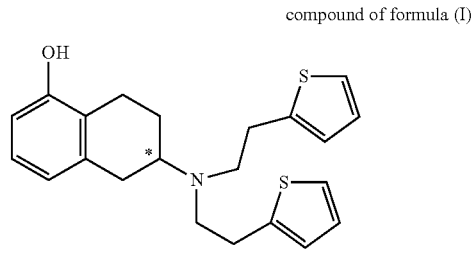 [SMILES: Oc1cccc2c1CCC(N(CCc1cccs1)CCc1cccs1)C2]

compound of formula (I)

wherein (*) represents a chiral center, and the compound of formula (I) is a R or S configuration or a racemic mixture.

2. A method for preparing a compound of formula (I) of claim 1, comprising:

reacting a compound of formula (II) with a compound of formula (III),

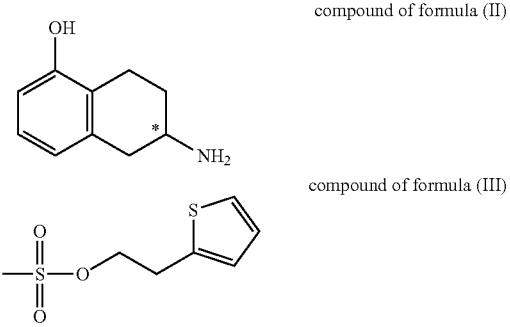

compound of formula (II)

compound of formula (III)

wherein the compound of formula (II) is a R or S configuration or a racemic mixture, and $R_1$ is methyl, trifluoromethyl, methylphenyl or nitrophenyl; and purifying the compound of formula (I).

3. The method of claim 2, wherein $R_1$ is 4-methylphenyl or 4-nitrophenyl.

4. The method of claim 3, wherein $R_1$ is 4-methylphenyl.

5. A method for determining an impurity in rotigotine or a preparation thereof, wherein the compound of formula (I) of claim 1 is used as a reference compound.

6. A method for determining the content of an impurity in rotigotine or a preparation thereof by high pressure liquid chromatography analysis, wherein the compound of claim 1 is used as a reference compound.

7. The method of claim 6, comprising:
preparing a reference solution of the compound of formula (I) in a pre-determined concentration;
preparing a test solution containing rotigotine or a preparation thereof;
obtaining HPLC chromatograms of the reference solution and the test solution by high pressure liquid chromatography analysis respectively;
comparing respective retention times in the HPLC chromatograms of the reference solution and the test solution to ascertain that the test solution contains the compound of formula (I) of claim 1; and
determining the content of the compound of claim 1 in rotigotine or the preparation thereof in weight percentage by an external standard method.

* * * * *